United States Patent
Wilson et al.

[11] Patent Number: 5,849,598
[45] Date of Patent: Dec. 15, 1998

[54] METHOD FOR TRANSFERRING MICRO QUANTITIES OF LIQUID SAMPLES TO DISCRETE LOCATIONS

[75] Inventors: Richard K. Wilson, Chesterfield, Mo.; Elaine R. Mardis, Troy, Ill.; Dimitrios A. Panussis, Creve Coeur, Mo.

[73] Assignee: Washington University, St. Louis, Mo.

[21] Appl. No.: 617,494

[22] Filed: Mar. 15, 1996

[51] Int. Cl.$^6$ .................................................... G01N 1/10
[52] U.S. Cl. ............................ 436/180; 436/179; 422/81; 422/100
[58] Field of Search ................................ 436/179, 177, 436/180; 422/65, 81, 100, 101

[56] References Cited

U.S. PATENT DOCUMENTS

| | | | |
|---|---|---|---|
| 3,193,358 | 7/1965 | Baruch | 422/65 |
| 3,269,800 | 8/1966 | Lukrec | 422/65 |
| 3,489,525 | 1/1970 | Natelson | 422/65 |
| 3,544,272 | 12/1970 | Vaills | 422/65 |
| 3,615,239 | 10/1971 | Jones | 422/65 |
| 3,677,091 | 7/1972 | Guigan | 422/100 X |
| 3,846,075 | 11/1974 | Cioffi | 422/81 |
| 3,929,411 | 12/1975 | Takano et al. | 422/81 X |
| 4,108,602 | 8/1978 | Hanson et al. | 422/81 X |
| 4,155,978 | 5/1979 | Naono et al. | 422/64 |
| 4,211,747 | 7/1980 | Gross | 422/81 |
| 4,219,530 | 8/1980 | Kopp et al. | 422/69 |
| 4,338,280 | 7/1982 | Ambers et al. | 422/68 |
| 4,601,881 | 7/1986 | Webster | 422/67 |
| 4,640,821 | 2/1987 | Mody et al. | 422/81 |
| 4,704,256 | 11/1987 | Hood et al. | 422/68 |
| 4,710,355 | 12/1987 | Ushikubo | 422/100 |
| 4,746,490 | 5/1988 | Saneii | 422/62 |
| 4,798,095 | 1/1989 | Itoh | 73/863.01 |
| 4,859,422 | 8/1989 | Qureshi et al. | 422/81 |
| 4,865,811 | 9/1989 | Newton et al. | 422/81 |
| 4,868,129 | 9/1989 | Gibbons et al. | 436/179 |
| 4,886,876 | 12/1989 | Zimmerman et al. | 530/383 |
| 4,946,795 | 8/1990 | Gibbons et al. | 436/179 |
| 4,962,044 | 10/1990 | Knesel et al. | 436/177 |
| 5,013,529 | 5/1991 | Itoh | 422/100 |
| 5,073,343 | 12/1991 | Hukuhara et al. | 422/67 |
| 5,108,928 | 4/1992 | Menard et al. | 436/43 |
| 5,112,575 | 5/1992 | Whitehouse et al. | 422/116 |
| 5,198,193 | 3/1993 | Bunce et al. | 422/100 |
| 5,223,222 | 6/1993 | Ricchio et al. | 422/63 |
| 5,316,728 | 5/1994 | Hayashi et al. | 422/70 |
| 5,380,495 | 1/1995 | Chang et al. | 422/131 |
| 5,405,585 | 4/1995 | Coassin | 422/100 |
| 5,445,037 | 8/1995 | Itoh | 73/864.25 |
| 5,453,382 | 9/1995 | Novotny et al. | 436/178 |
| 5,565,171 | 10/1996 | Dovichi et al. | 422/68.1 |

OTHER PUBLICATIONS

Hewick et al., A gas–liquid Solid phase Peptide and Protein Sequenator, the Journal of Biological Chemistry, vol. 256, No. 15, pp. 7990–7997, Aug. 10, 1981.

*Primary Examiner*—Harold Y. Pyon
*Attorney, Agent, or Firm*—Howell & Haferkamp, L.C

[57] ABSTRACT

A method for simultaneously and uniformly transferring micro quantities of liquid from a first plurality of separate cells to a second plurality of separate cells. Each of the first plurality of separate cells contain a liquid sample. Intake ends of a plurality of conduits are inserted into the first cells so that the intake ends of the conduits are immersed in the liquid samples. The conduits further including discharge ends. The discharge ends of the conduits are aligned with the second plurality of cells. A pressure differential is created between the first plurality of cells and the second plurality of cells to cause micro quantities of the liquid samples to simultaneously and uniformly flow through their respective conduits and to the second plurality of cells.

12 Claims, 7 Drawing Sheets

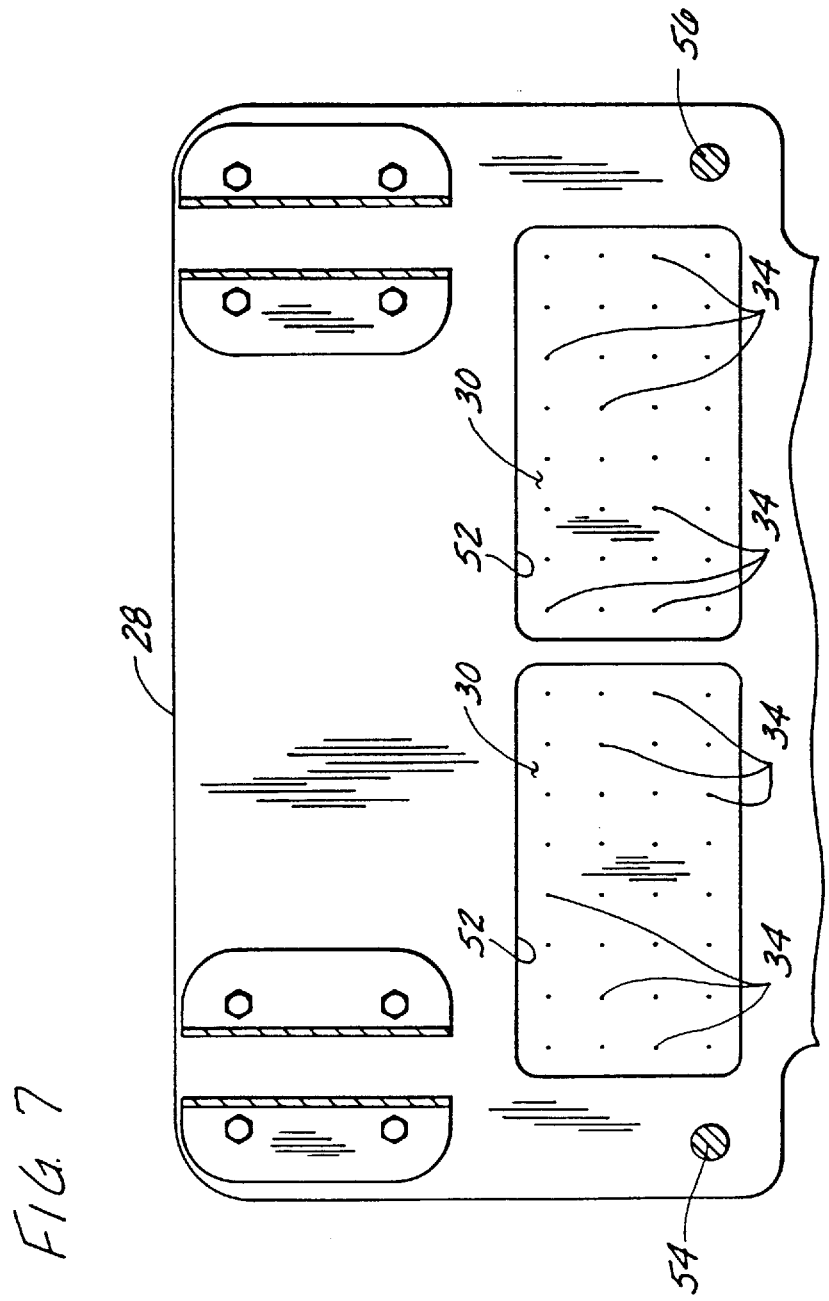

METHOD FOR TRANSFERRING MICRO QUANTITIES OF LIQUID SAMPLES TO DISCRETE LOCATIONS

REFERENCE TO GOVERNMENT SUPPORT

This invention was made with government support under Grant No. HG00956 awarded by the National Institutes of health. The government has certain rights in the invention.

BACKGROUND OF THE INVENTION

This invention relates to a method of and apparatus for transferring micro quantities of liquid samples from a first plurality of separate cells to a second plurality of separate cells.

Micro quantities (e.g., 1–50 $\mu$l) of DNA sequencing reaction products are commonly placed in destination wells formed in polyacrylamide or agarose slab gels for separation and detection in electrophoretic devices such as DNA sequencers. Such slab gels usually have an array of destination wells (e.g., sixty-four or ninety-six) for simultaneous separation and detection of a like number of liquid samples containing DNA.

The process of transferring liquid samples to gel wells has typically been a manually performed task. Conventionally, this is performed one sample at a time using a variable volume pipettor. If the liquid samples are transferred to a polyacrylamide slab gel contained between two closely spaced glass plates, the pipettor has been fitted with a suitable tip for facilitating placement of the sample between the plates. Single sample transfers have also been performed with glass syringes of one to five micro-liter volume capacity, and with drawn-out glass capillary tubing attached to a mouth pipettor. Pipettors capable of multiple sample loading have been employed for manual use. These pipettors include an array of eight or twelve glass syringes with their centers equally spaced and their plungers coupled together.

With such manual sample transfers, the operator must manually transfer one, eight or twelve different samples at a time to a like number of discrete locations, and then repeat this process until fluid transfers have been made to the desired number of destination wells (e.g., ninety-six wells), one at a time, up to ninety-six different samples to ninety-six discrete destination wells. In the case of polyacylimide gels, the manual liquid sample transfer is done one sample at a time. In the case of agarose gels, the multiplicity of manual sample transfer cannot exceed the number of syringes of the manual pipettors, provided the wells in the gel have been formed accordingly. A difficulty associated with such transfers is that they are prone to operator error. For example, the operator might inadvertently transfer the same sample to two or more destination wells, switch two samples, or skip a well. Depending on the severity of the error, a remedy might take several hours to correct because in certain cases the DNA samples would need to be re-processed. Another difficulty associated with such transfers is the time required to serially transfer the DNA samples to all destination wells. The time lag between loading of the first and last destination wells often results in diffusion-related band broadening. Moreover, such manual transfers often result in different volumes of fluid in the destination wells. In other words, some destination wells might end up containing a greater or lesser volume of fluid.

An automatic gel loading device exists which employs a simple x-y plotter for transferring a single sample using a glass syringe having a flexible fused silica capillary tip. Although loading destination wells with such an automated gel loading device reduces the chances of operator error, use of such a device is also subject to a time lag between loading of the first and last destination wells and is therefore subject to diffusion-related band broadening. This device is also costly.

SUMMARY OF THE INVENTION

Among the several objects of the present invention may be noted the provision of an improved method and apparatus for transferring micro quantities of liquid samples to an array of destination cells (or locations); the provision of such a method and apparatus which minimize operator error; the provision of such a method and apparatus which minimize time lag between loading of first and last cells of the array of destination cells; the provision of such a method and apparatus which minimize such time lag by simultaneously transferring all liquid samples to their destination wells; the provision of such a method and apparatus which ensure the transfer of substantially equal volumes of liquid to each of the destination cells; the provision of such a method and apparatus which are easy to employ; and the provision of such an apparatus which is of relatively simple construction.

In general, a method of the present invention results in simultaneous transfer of micro quantities of liquid from a first plurality of separate cells to a second plurality of separate cells. Each of the first plurality of separate cells contains a liquid sample. The method comprises placing intake ends of a plurality of conduits into the first cells so that the intake ends of the conduits are immersed in the liquid samples, aligning discharge ends of the conduits with the second plurality of cells, and creating a gas pressure differential between the first plurality of cells and the second plurality of cells to cause micro quantities of the liquid samples to simultaneously flow through their respective conduits and to the second plurality of cells.

Another aspect of the present invention is an apparatus for simultaneously transferring micro quantities of a plurality of liquid samples from a plurality of separate liquid containing cells to a second plurality of discrete locations. The apparatus comprises a plurality of conduits each having an intake end and a discharge end. The intake ends of the conduits are configured for extending into the liquid containing cells and in fluid communication with the liquid samples. The discharge ends of the conduits are configured for alignment with the second plurality of discrete locations. The apparatus further includes means for simultaneously and uniformly pressurizing all of the first plurality of separate liquid containing cells with a gas to pressurize the liquid samples and thereby cause at least a portion of each of the liquid samples to flow through their respective conduits and to the second plurality of discrete locations.

In another aspect of the invention, an apparatus for simultaneously transferring micro quantities of a plurality of liquid samples from a plurality of separate liquid containing cells to a second plurality of discrete locations includes a pressure chamber configured for enclosing the cells. Intake ends of conduits are within the pressure chamber and discharge ends of the conduits are exterior of the pressure chamber. The apparatus further includes a pressure inducing mechanism configured for introducing gas into the pressure chamber for simultaneously and uniformly pressurizing the plurality of cells to thereby cause at least a portion of each of the liquid samples to flow through their respective conduits and to the second plurality of discrete locations.

Other objects and features will be in part apparent and in part pointed out hereinafter.

BRIEF DESCRIPTION OF THE DRAWINGS

FIG. 7 is a fragmented cross-sectional view taken along the plane of line 7—7 of FIG. 4 showing the underside of the pressure block and the inside of the pressure chamber.

Corresponding reference characters indicate corresponding parts throughout the several views of the drawings.

DESCRIPTION OF THE PREFERRED EMBODIMENTS

Figure 1:
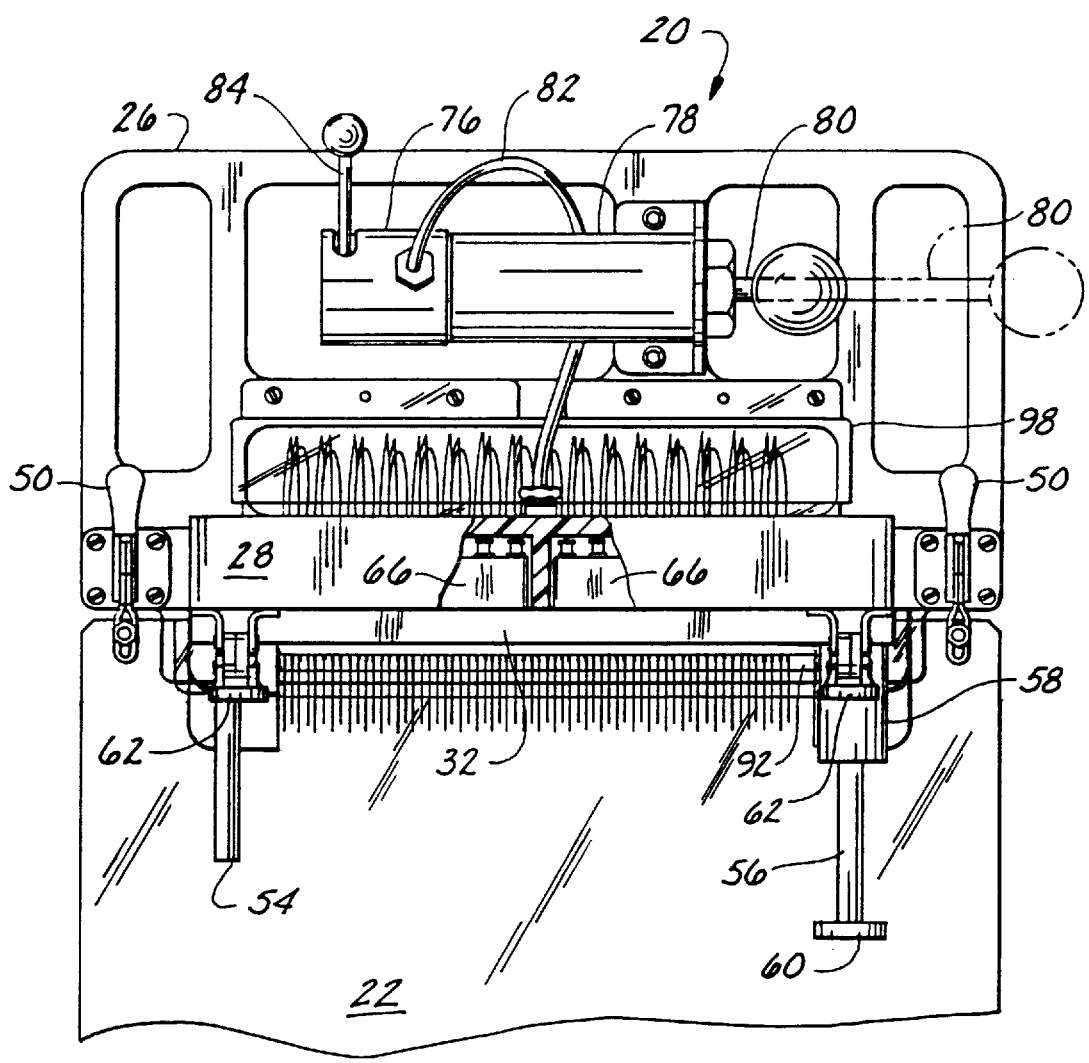
FIG. 1 is a front elevational view of an electrophoresis gel loading apparatus of the present invention with portions of a pressure block broken away to show the inside of a pressure chamber.

Referring now to the drawings, and first more particularly to FIGS. 1–4, an electrophoresis gel loading apparatus of the present invention is indicated in its entirety by the reference numeral 20. The gel loading apparatus 20 facilitates the simultaneous transfer of micro quantities of a plurality of liquid samples from a plurality of separate liquid containing cells (e.g., a plurality of sample tubes) to a like plurality of discrete locations (e.g., a plurality of destination wells between parallel front and back plates of glass 22, 24 of a conventional vertical slab gel electrophoretic device). The gel loading apparatus 20 comprises a vertical support plate 26, a pressure block 28 mounted on the support plate and defining a pressure chamber 30 therein, and a slidable pressure tray 32 engageable with an underside of the pressure block for closing the pressure chamber. A plurality of liquid conveying conduits (e.g., capillaries 34) have first ends 36 (e.g., intake ends) inside the pressure chamber 30 and second ends 38 (e.g., discharge ends) outside the pressure chamber. As discussed in greater detail below, the second ends 38 of the capillaries 34 are preferably arranged for insertion between the plates of glass 22, 24 and into destination wells 21 (FIG. 5). As also discussed below, the gel loading apparatus 20 is configured so that creation of a positive pressure in the pressure chamber 30 causes liquid to flow from the first ends 36 of the capillaries 34 to the second ends 38, and creation of a negative pressure therein causes liquid to flow from the second ends of the capillaries to the first ends.

Two spaced-apart holding fingers 40 are secured to the bottom edge margin of the backside of the vertical support plate 26 for holding the gel loading apparatus 20 on the electrophoretic device. In particular, the holding fingers 40 are configured for engaging the upper portions of the front and back glass plates 22, 24. The glass plates 22, 24 have a small gap between them filled with a suitable gel, such as polyacrylamide. The back glass plate 24 has a cut-out 44 (FIG. 5) formed at its top. Each holding finger 40 includes a downwardly facing surface 46 engageable with the upper edge of the back glass plate 24, and a forwardly facing surface 48 engageable with a rearwardly facing side of the front glass plate 22. Engagement of the upper edge of the back glass plate 24 by the downwardly facing surfaces 46 of the holding fingers 40 prevents downward movement of the gel loading apparatus 20 relative to the glass plates.

Two stabilizing clamps 50 are mounted on the support plate 26 and engageable with the forwardly facing side of the front glass plate 22 for releasably pressing the front glass plate between the clamp 50 and the forwardly facing surfaces 48 of the holding fingers 40 to thereby prevent forward and rearward movement of the gel loading apparatus 20 relative to the glass plates 22, 24. As best shown in FIG. 5, the outer faces of the holding fingers 40 are preferably spaced apart a distance less than the width of the cut-out 44 of the back glass plate 24. Preferably, the outer face of the right holding finger 40 contacts the inner face at the right ear of the cut-out 44 of the back glass plate 24 so that the second ends 38 of the capillaries align with the destination wells 21 in the gel 40. Thus, the holding fingers 40 and clamps 50 secure the gel loading apparatus 20 to the glass plates 22, 24 and properly orient and align the gel loading apparatus on the electrophoretic device.

Figure 2:
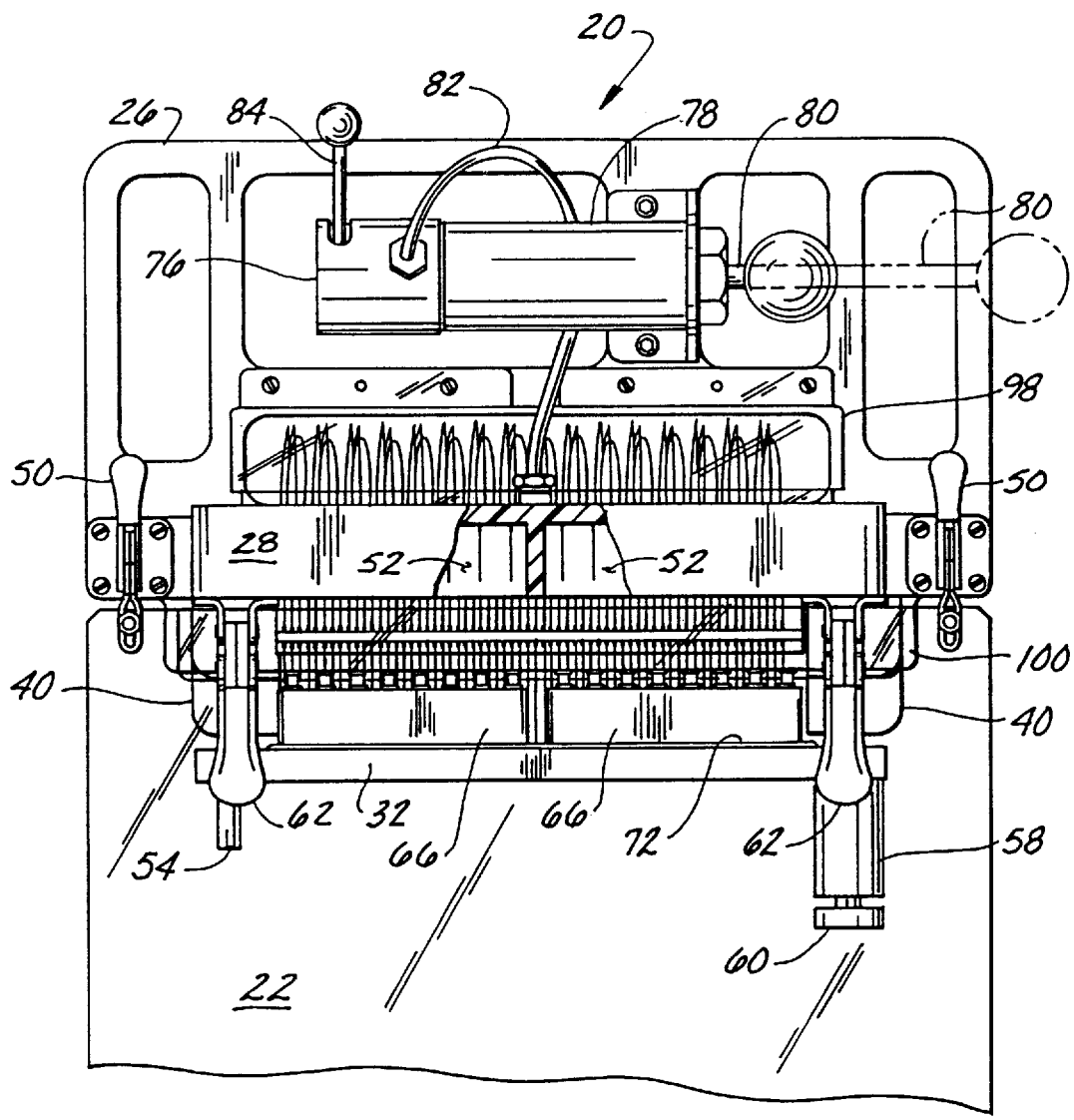
FIG. 2 is a front elevational view of the electrophoresis gel loading apparatus of FIG. 1 showing a moveable pressure tray of the apparatus in a lowered position below the pressure chamber.

The pressure block 28 is preferably of a suitable polymeric material such as the type sold under the trademark Delrin, available from E. I. duPont de Nemours Co. Inc. The pressure chamber 30 comprises two compartments 52 which are in fluid communication with each other via a suitable passageway (not shown). Preferably, the passageway is sufficiently large so that a change in pressure in one compartment 52 will result in a rapid like change in pressure in the other. Two parallel, vertical rods 54, 56 are secured at their upper ends to the pressure block 28 for guiding the pressure tray 32 between a raised position (FIGS. 1 and 3) and a lowered position (FIGS. 2 and 4). In its raised position, the pressure tray 32 abuts against the underside of the pressure block 28 for closing the pressure chamber 30. In its lowered position, the pressure tray 32 is spaced below the pressure block 28 for providing access to the top side of the pressure tray 32 and the inside of the pressure chamber 30. Preferably, a bearing cylinder 58 is secured to the underside of the pressure tray 32 and is slidably connected to rod 56 for facilitating up and down movement of the pressure tray 32 relative to the pressure block 28. Also preferably, a stopper 60 is fixed to the lower end of rod 56 for limiting downward movement of the pressure tray 32. Two tray-holding clamps 62 are mounted to the underside of the pressure block 28 and engageable with the underside of the pressure tray 32 for releasably locking the pressure tray in its raised position.

The pressure tray 32 preferably has two recessed areas 64 (FIG. 6) sized for receiving two removable tube racks 66. Each tube rack 66 preferably has thirty-two through bores for receiving thirty-two liquid-containing sample tubes 70. A gasket 72 is positioned in a groove 74 (FIG. 6) circumscribing the two recessed areas 64 of the pressure tray 32. The gasket 72 provides a gas-tight seal between the pressure tray 32 and the pressure block 28 when the pressure tray is in its raised position. The pressure tray 32 and pressure block 28 are shaped and configured so that a tube rack 66 is positioned in each compartment 52 of the pressure chamber 30 when the pressure tray is in its raised position.

A hand pump 76 is mounted on the vertical support plate 26 via a bracket. Preferably, the hand pump 76 is a Stainless Steel Body Air Cylinder available from Bimba Mfg. Co., Monee, Ill. As discussed in greater detail below, the hand pump 76 constitutes means for pressurizing and evacuating the pressure chamber 30. The hand pump 76 includes a pump cylinder 78, a plunger (not shown) within the pump cylinder, and a plunger rod 80 secured to the plunger. The plunger rod 80 is moveable relative to the pump cylinder 78 between a compression position (shown in solid in FIGS. 1 and 2) and an extended position shown in phantom in FIGS. 1 and 2) for facilitating reciprocating movement of the plunger in the pump cylinder. Preferably, a spring (not shown) is positioned in the pump cylinder 78 for biasing the plunger rod 80 in the compression position. A suitable hose 82 provides fluid communication between the pump cylinder 78 and the pressure chamber 30. The pump 76 further includes a valve lever 84 moveable between a vent position (shown in phantom in FIGS. 3 and 4) and a port position (shown in solid in FIGS. 3 and 4) for opening and closing a suitable valve (not shown). When the valve lever 84 is in its vent position, the pump cylinder 78 is open to atmosphere. When the valve lever 84 is in its port position, the pump cylinder 78 is closed to atmosphere. Moving the plunger rod 80 to its extended position increases the effective air volume of the system (i.e., the volume of air in both the pressure chamber 30 and pump cylinder 78) by the cross-sectional area of the plunger times the plunger stroke. Turning the valve lever 84 to its port position seals the system from atmosphere. When the plunger rod 80 is released, the spring causes the plunger rod 80 and plunger to move to the compression position which in turn causes a positive pressure increase in the pressure chamber 30. This pressure increase provides the driving force for the liquid transfer. This driving force may be quickly interrupted (i.e., the pressure in the chamber 30 may be quickly released) at any time by moving the valve lever 84 to its vent position.

Although the hand pump 76 constitutes the preferred means for pressurizing and evacuating the pressure chamber 30, it is to be understood that other means may be employed without departing from the scope of this invention. For example, the hand pump 76 could be replaced with an electric pump, a pressurized gas cylinder, or any other source of gas pressure.

The capillaries 34 are preferably fused silica capillary tubes with polyimide coating, such as those available from Polymicro Technologies, Inc., Phoenix, Ariz. 85023. The capillaries 34 extend through the pressure block 28 so that the first ends 36 (e.g., intake ends) of the capillaries are within the pressure chamber 30 and the second ends 38 (e.g., discharge ends) of the capillaries are exterior of the pressure chamber 30. The capillaries 34 are secured to the pressure block 28 by relatively short, rigid sleeves 86 (FIG. 6) extending through and sealed to the pressure block 28. Preferably, the gel loading apparatus 20 includes sixty-four capillaries 34 (FIG. 7, thirty-two of which extend into one compartment 52 and the other thirty-two of which extend into the other compartment. The first ends 36 of the capillaries 34 are suitably spaced and arranged to align with and be surrounded by the sample tubes 70 when the pressure tray 32 is in its raised position. Because of the locations of the first ends 36 of the capillaries 34 within the pressure chamber 30, these ends penetrate the liquid surfaces of liquid samples 90 contained in the sample tubes 70 and are immersed in the liquid samples cleaning the bottom of the sample tubes by a small margin (e.g., approximately 0.5 mm).

Figure 5:
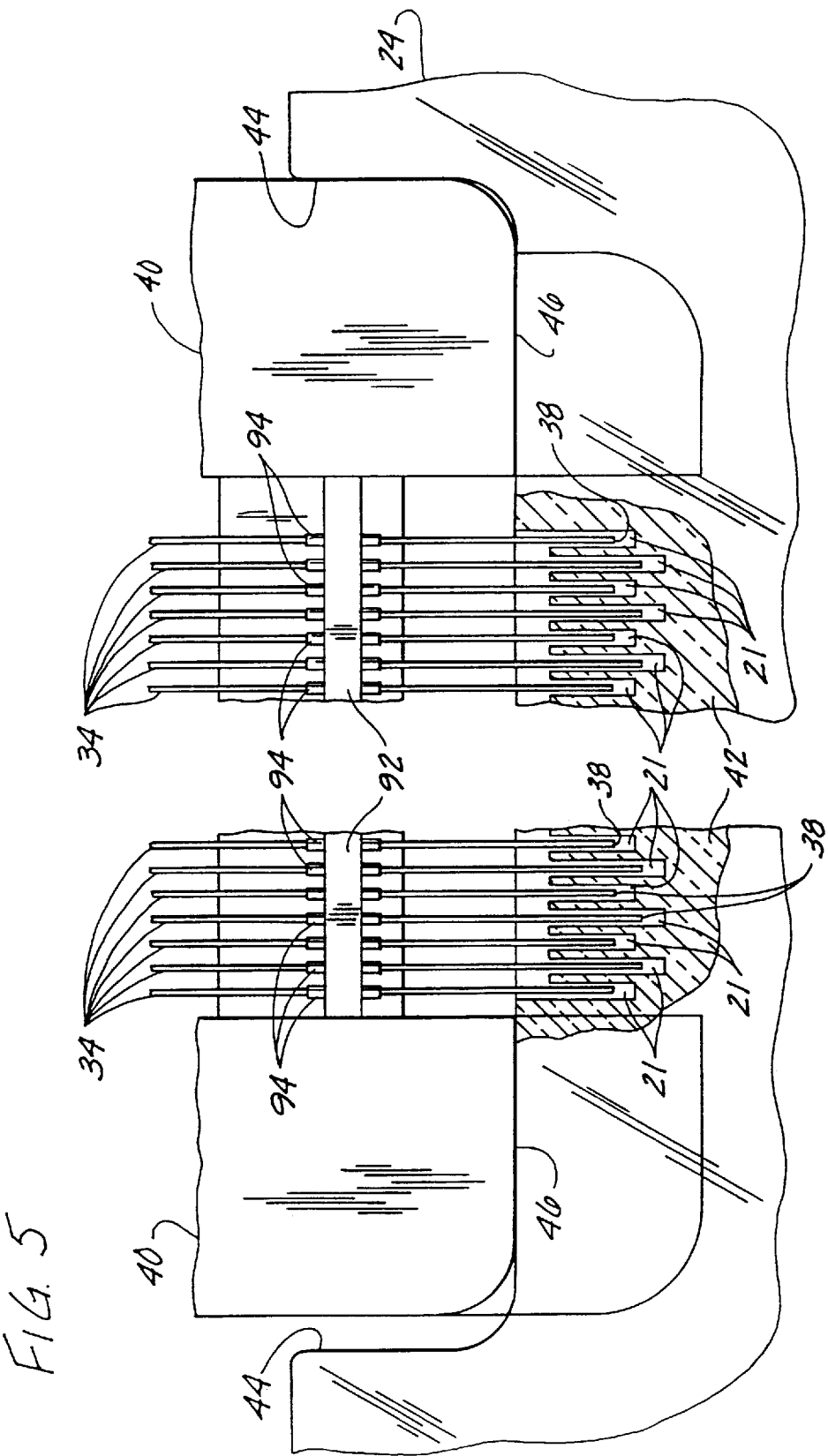
FIG. 5 is a fragmented cross-sectional view taken along the plane of line 5—5 of FIG. 3.
Figure 6:
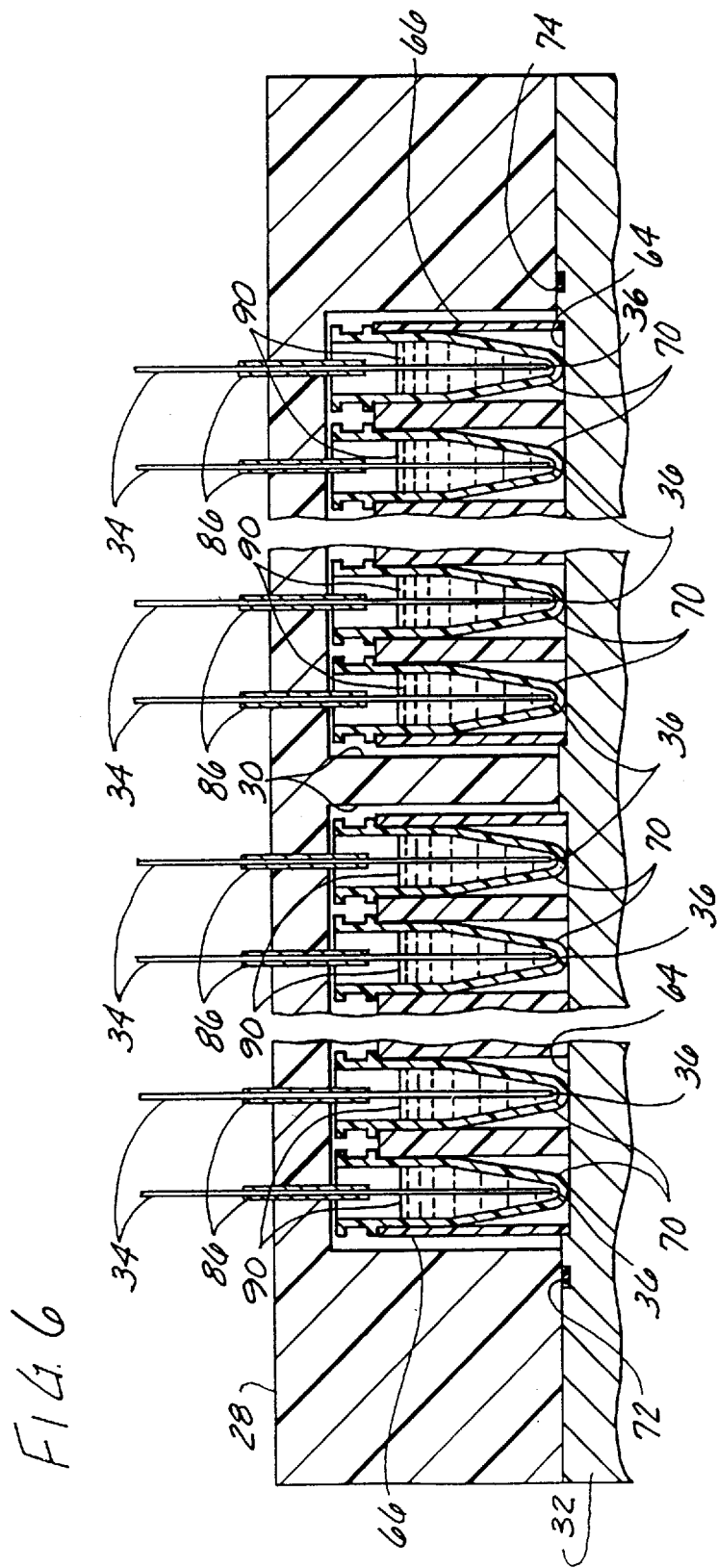
FIG. 6 is a cross-sectional view taken along the plane of line 6—6 of FIG. 3.

Referring to FIG. 6, pressurization of the pressure chamber 30 creates a simultaneous and uniform positive pressure over the surface of the liquid samples 90. Because all sixty-four of the liquid samples 90 are exposed to the increased pressure in the pressure chamber 30 and because the pressure in the pressure chamber is uniform throughout, every liquid sample is subject to the same pressure at the same time. This pressurization causes the liquid samples 90 to simultaneously flow from their sample tubes 70 and through their capillaries 34. Preferably, all of the capillaries 34 have substantially the same inside diameter (e.g., approximately 0.100 mm) and substantially the same length (e.g., 160 mm) so that equal pressurization of the liquid samples 90 causes liquid from all samples to simultaneously flow through their respective capillaries 34 at substantially the same flow rate. Preferably, each of the capillaries 34 is sized and the pressurization of the pressure chamber 30 is selected to cause a flow rate therethrough of between approximately 1 $\mu$l/min and 150 $\mu$l/min. Also, because of the capillaries 34, pump 76, and pressure chamber 30, the flow through all capillaries may be stopped simultaneously so that equal micro quantities of liquid may be dispensed to each of the destination wells 21 (FIG. 5). The flow may be stopped by moving the lever 84 to its vent position to thereby relieve the pressure in the pressure chamber 30. It is envisioned that for use with most electrophoretic devices, it is desirable to dispense approximately 1 $\mu$l to 50 $\mu$l of liquid into each destination well, and more particularly, to dispense between 1 $\mu$l and 10 $\mu$l. After the desired amount of liquid has been dispensed, the flow is stopped by manually moving the lever 84 to its vent position.

Although the gel loading apparatus 20 of the present invention has been described as having sixty-four capillaries 34, it is to be understood that the apparatus 20 could have more capillaries (e.g., ninety-six) or fewer capillaries without departing from the scope of this invention.

Figure 3:
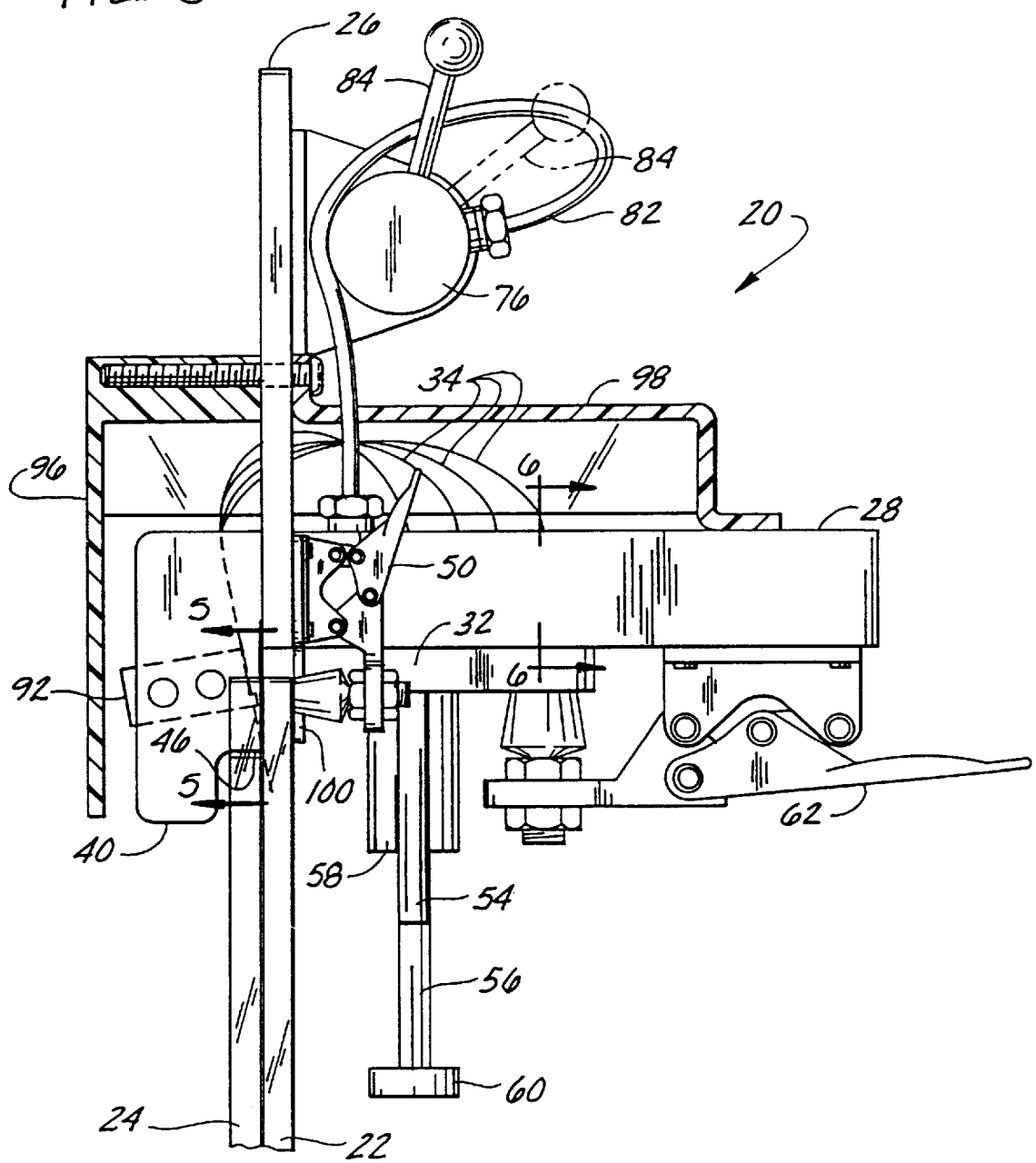
FIG. 3 is a side elevational view of the electrophoresis gel loading apparatus of FIG. 1 with the moveable pressure tray in a raised position and with portions of the pressure block broken away to show the pressure chamber.
Figure 4:
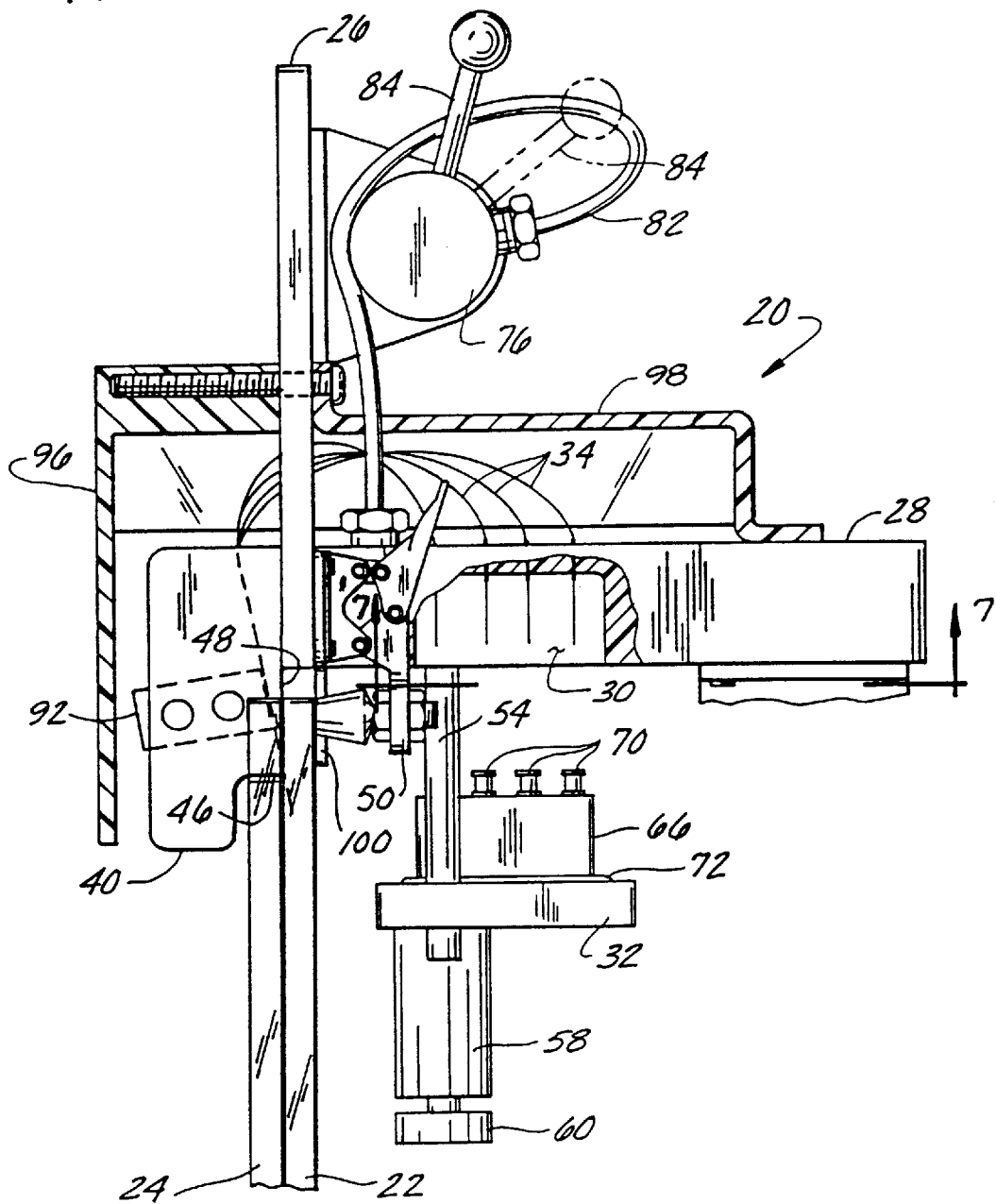
FIG. 4 is a side elevational view of the electrophoresis gel loading apparatus of FIG. 3 with the moveable pressure tray in a lowered position and with portions of the pressure block broken away to show detail.

Referring now to FIGS. 3–5, a capillary array holder 92 extends between and is secured at its ends to the holding fingers 40. Capillary receiving sleeves 94 extend through and are secured to the capillary array holder 92. The capillaries 34 extend through and are held by the sleeves 94 with the second ends 38 (e.g., discharge ends) of the capillaries spaced below the array holder 92. Preferably, the second ends 38 of the capillaries 34 are coplanar for facilitating insertion of the capillaries in the gap between the glass plates 22, 24. Also preferably, the array holder holds the capillaries 34 at a slight incline (see FIGS. 3 and 4) for further facilitating insertion of the capillaries in the gap between the glass plates 22, 24. As shown in FIG. 5, a plurality (e.g., sixty-four) of destination wells 21 are formed in the gel 42. When the gel loading apparatus 20 is properly positioned on the glass plates 22, 24, the second ends 38 of the capillaries 34 align with and extend into the destination wells 21. Subsequent pressurization of the pressure chamber 30 causes flow through the capillaries 34 and into the destination wells.

Referring again to FIGS. 1–4, the gel loading apparatus further includes transparent acrylic shields for protecting the fragile capillaries. In particular, a back shield 96 is secured to the support plate 26 and extends over the rear of the gel loading apparatus 20. Upper and lower front shields 98, 100 are secured to the front of the support plate. The shields protect the capillaries without hindering operation of the apparatus 20.

In operation, the sample tubes 70 contain a small volume of liquid (e.g., liquid samples containing DNA), and the sample tubes and tube racks are placed on the pressure tray 32. The pressure tray 32 is then moved to its raised position and the tray-holding clamps 62 are positioned to press the tray against the pressure block 28. With the pressure tray 32 so positioned, the first ends 36 of the conduits are immersed in the liquid samples 90. The gel loading apparatus 20 is then positioned on the glass plates 22, 24 so that the second ends 38 of the capillaries 34 extend down into the destination wells 21 between the glass plates. The hand pump 76 is then actuated to pressurize the pressure chamber 30. Pressurization of the pressure chamber 30 pressurizes the surface of each liquid sample 90 which causes a pressure differential between the first and second ends 38 of the capillaries 34. This pressure differential causes the liquid samples 90 to flow into the first ends 36 of the capillaries 34, out the second ends 38 of the capillaries 34 and into the destination wells 21 of the gel 42. This liquid preferably flows through each capillary 34 at a rate of between approximately 1 $\mu$l/min and 150 $\mu$l/min, and more preferably, at a rate of between approximately 2 $\mu$l/min and 50 $\mu$l/min. After a desired quantity of each liquid sample has been dispensed to its associated destination well 21, the valve lever 84 is moved to its vent position to relieve the pressure in the pressure chamber 30 and thereby stop the flow. The valve lever 84 is moved to its vent position preferably after at least approximately 1 $\mu$l has been discharged from each capillary 34 but before approximately 50 $\mu$l of the liquid have been discharged, and more preferably before approximately 10 $\mu$l have been discharged. Thus, equal quantities of a plurality of different liquids are simultaneously dispensed to a like plurality of different locations in a quick and easy manner.

The gel loading apparatus 20 may also be used for transferring a plurality of liquids from the second ends 38 of the capillaries 34 to the first ends 36. When operated in this manner, the second ends 38 constitute intake ends and the first ends 36 constitute discharge ends. To accomplish this, each of the second ends 38 of the capillaries 34 must be immersed in a liquid and the chamber 30 must be evacuated so that the pressure at the first ends 36 of the capillaries is less than the pressure at the second ends 38 of the capillaries. The negative pressure in the chamber 30 draws liquid from the second ends 38 of the capillaries 34 and into the sample tubes 70. Negative pressure in the chamber 30 is created by first moving the plunger rod 80 to its compression position and moving the valve lever 84 to its vent position to relieve any pressure in the chamber 30. The valve lever 84 is then moved to its port position and the plunger rod 80 is moved to its extended position. Because moving the plunger rod 80 to its extended position effectively increases the volume of the system without increasing the mass of air in the system, the pressure in the pressure chamber 30 is reduced. Thus, the pump 76 may be used for increasing or decreasing the pressure in the chamber 30.

Although the apparatus 20 has been described as being configured to simultaneously dispense a plurality of liquids to an electrophoretic device, it is to be understood that the apparatus is not limited to such use. In other words an apparatus and/or method of the present invention may be employed whenever it is desirable to simultaneously transfer micro quantities of liquid from one location to another.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense. It is intended that the invention shall be limited solely by the scope of the claims.

What is claimed is:

1. A method of simultaneously transferring quantities of liquid from a first plurality of separate cells to a second plurality of separate cells, each of the first plurality of separate cells containing a liquid sample, the method comprising:

placing intake ends of a plurality of capillaries into the first cells so that the intake ends of the capillaries are immersed in the liquid samples the capillaries further Including discharge ends;

aligning the discharge ends of the capillaries with the second plurality of cells;

sealing one of said first and second plurality of cells in a pressure chamber, the other of said first and second plurality of cells being exterior of the pressure chamber; and creating a pressure differential between the first plurality of cells and the second plurality of cells to cause quantities of the liquid samples to simultaneously flow through their respective capillaries and to the second plurality of cells, the step of creating a pressure differential comprising inducing a change of gas pressure in the pressure chamber so that the gas pressure in the pressure chamber is different from gas pressure in the other of said first and second plurality of cells.

2. A method as set forth in claim 1 wherein:

the discharge ends of the capillaries are within the pressure chamber;

the step of sealing one of said first and second plurality of cells in a pressure chamber comprises sealing the second plurality of cells in the pressure chamber; and the step of inducing a change of gas pressure in the pressure chamber comprises decreasing gas pressure in the pressure chamber to a gas pressure less than gas pressure in the first plurality of cells to draw liquid through the capillaries and into the first plurality of cells.

3. A method as set forth in claim 1 wherein:

the intake ends of the capillaries are within the pressure chamber and the liquid samples have surfaces exposed to the interior of the pressure chamber;

the step of sealing one of said first and second plurality of cells in a pressure chamber comprises sealing the first plurality of cells in the pressure chamber; and the step of inducing a change of gas pressure in the pressure chamber comprises increasing gas pressure in the pressure chamber to a pressure greater than gas pressure in the second plurality of cells to force liquid through the capillaries and into the second plurality of cells.

4. A method as set forth in claim 1 further comprising the step of simultaneously stopping flow of fluid through the capillaries after at least approximately 1 microliter has been discharged from each capillary but before approximately 50 microliters of the liquid has been discharged from each conduit.

5. A method as set forth in claim 1 further comprising the step of simultaneously stopping flow of fluid through the capillaries after at least approximately 1 microliter has been discharged from each capillaries but before approximately 10 micraliters of the liquid has been discharged from each conduit.

6. A method of simultaneously transferring quantities of liquid from a first plurality of separate cells to a second plurality of separate cells, each of the first plurality of separate cells containing a liquid sample, the method comprising:

placing intake ends of a plurality of conduits into the first cells so that the intake ends of the conduits are immersed in the liquid samples, the conduits further including discharge ends;

aligning the discharge ends of the conduits with the second plurality of cells;

sealing one of said first and second plurality of cells in a pressure chamber, the other of said first and second plurality of cells being exterior of the pressure chamber; and creating a pressure differential between the first plurality of cells and the second plurality of cells to cause quantities of the liquid samples to simultaneously flow through their respective conduits and to the second plurality of cells;

the step of creating a pressure differential comprising simultaneously pressurizing the first plurality of cells with a gas to pressurize the liquid samples and cause micro quantities of the liquid samples to flow through their respective conduits and to the second plurality of cells the step of simultaneously pressurizing the first plurality of cells comprising simultaneously pressurizing each of the first plurality of cells to substantially the same pressure, the step of simultaneously pressurizing the plurality of cells comprising pressurizing the cells to pressures suitable for causing the liquid to be dispensed from the discharge end of each conduit at a rate of between approximately 1 $\mu$l/min and 150 $\mu$l/min.

7. A method as set forth in claim 5 wherein the intake ends of the conduits are within the pressure chamber and the discharge ends of the conduits are exterior of the pressure chamber, the liquid samples having surfaces exposed to the interior of the pressure chamber, and wherein the step of simultaneously pressurizing the plurality of cells comprises pressurizing gas within the pressure chamber.

8. A method as set forth in claim 6 wherein the second plurality of cells comprises a plurality of gel wells for use in an electrophoretic device and wherein the step of aligning the discharge ends of the conduits with the second plurality of cells comprises aligning the discharge ends of the conduits with the gel wells.

9. A method of simultaneously transferring quantities of liquid from a first plurality of separate cells to a second plurality of separate cells, each of the first plurality of separate cells containing a liquid sample, the method comprising:

placing intake ends of a plurality of conduits into the first cells so that the intake ends of the conduits are immersed in the liquid samples, the conduits further including discharge ends;

aligning the discharge ends of the conduits with the second plurality of cells;

sealing one of said first and second plurality of cells in a pressure chambers the other of said first and second plurality of cells being exterior of the pressure chamber;

creating a pressure differential between the first plurality of cells and the second plurality of cells to cause quantities of the liquid samples to simultaneously flow through their respective conduits and to the second plurality of cells, the step of creating a pressure differential comprising inducing a change of gas pressure in the pressure chamber so that the gas pressure in the pressure chamber is different from gas pressure in the other of said first and second plurality of cells; and simultaneously stopping flow of fluid through the conduits after at least approximately 1 microliter has been discharged from each conduit but before approximately 50 microliters of the liquid has been discharged from each conduit.

10. A method as set forth in claim 9 wherein:

the discharge ends of the conduits are within the pressure chamber;

the step of sealing one of said first and second plurality of cells in a pressure chamber comprises sealing the second plurality of cells in the pressure chamber; and the step of inducing a change of gas pressure in the pressure chamber comprises decreasing gas pressure in the pressure chamber to a gas pressure less than gas pressure in the first plurality of cells to draw liquid through the conduits and into the first plurality of cells.

11. A method as set forth in claim 9 wherein:

the intake ends of the conduits are within the pressure chamber and the liquid samples have surfaces exposed to the interior of the pressure chamber;

the step of sealing one of said first and second plurality of cells in a pressure chamber comprises sealing the first plurality of cells in the pressure chamber; and the step of inducing a change of gas pressure in the pressure chamber comprises increasing gas pressure in the pressure chamber to a pressure greater than gas pressure in the second plurality of cells to force liquid through the conduits and into the second plurality of cells.

12. A method as set forth in claim 9 further comprising the step of simultaneously stopping flow of fluid through the conduits after at least approximately 1 microliter has been discharged from each conduit but before approximately 10 microliters of the liquid has been discharged from each conduit.

* * * * *